US006235311B1

(12) United States Patent
Ullah et al.

(10) Patent No.: US 6,235,311 B1
(45) Date of Patent: May 22, 2001

(54) PHARMACEUTICAL COMPOSITION CONTAINING A COMBINATION OF A STATIN AND ASPIRIN AND METHOD

(75) Inventors: Ismat Ullah; Nemichand B. Jain, both of Cranbury, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/040,794

(22) Filed: Mar. 18, 1998

(51) Int. Cl.⁷ .............................. A61K 9/24; A61K 9/28; A61K 9/26
(52) U.S. Cl. ........................... 424/472; 424/470; 424/474
(58) Field of Search ............................. 424/452, 458–59, 424/474, 469, 470, 472, 489–90

(56) References Cited

U.S. PATENT DOCUMENTS

| H1286 | * | 2/1994 | Eisman et al. . |
| 5,225,202 | * | 7/1993 | Hodges et al. . |
| 5,238,686 | * | 8/1993 | Gcotel et al. . |

FOREIGN PATENT DOCUMENTS

| WO93/13801 | 7/1993 | (WO) . |
| WO98/11896 | 3/1998 | (WO) . |

OTHER PUBLICATIONS

Revue Mecicale de Liege, 1996, 51/10 (663–669.
"Pravastatin's MI preventive effect, carvedilo's mortality benefit are among top newsmaker", Formulary, vol. 31, Jan. 1998, 65–68.
Veinot, J.P. et al, "The effects of lovastatin on neointimal hyperplasia following injury in a porcine coronary artery model", Can. J. Cardiol. vol. 12(1), 65–70.
Bjelajac, A. et al, "Prevention and Regression of Atherosclerosis: Effects of HMG–CoA Reductase Inhibitors", Ann. Pharcacother., 30, No. 11, 1996, 1304–1315.
Pedersen, T.R. et al, "Safety and Tolerability of Cholesterol Lowering With Simvastatin During 5 Years in the Scandinavian Simvastatin Survival Study", Arch. Inter. Med., vol. 156, No. 18, 1996, 2085–2092.
Sacks, F.M., et al, "The Effect of Pravastatin on Coronary Events After Myocardial Infarction in Patients with Average Cholesterol Levels", N. Engl. J. Med. 335, No.14, 1001–1009, 1996.
J. Am. Coll. Cardiol. 27, No. 2, Suppl. A, 413A, 1996.
Biorheology, vol. 32, No. 2, 2–3, 1995, 264.
American Family Physician, 1995, 52/3, (761, 766, 768, 775).
Circulation, 92, No. 8, Suppl. I–196, 1995.
Pitt, B. et al, "Pravastatin Limitation of Atherosclerosis in the Coronary Arteries (PLAC I): Reduction in Atherosclerosis Progression and Clinical Events", JACC vol. 26, No. 5, 1995, 1133–39.
Watts, G.R., "Simvastatin decreases the hepatic secretion of very–low–density lipoprotein apolipoprotein B–100 in heterozygous familial hypercholesterolaemia: pathophysiological and therapeutic implications", Eur. J. Clin. Invest. 25, No. 8, 559–67, 1995.
Sacks, F.M. et al, "Baseline Characteristics in the Cholesterol and Recurrent Events (CARE) Trial of Secondary Prevention in Patients With Average Serum Cholesterol Levels", Amer. J. of Cardiology, 1995, 75/8, 621–623.
Brown, G. et al, "Regression of Coronary Artery Disease as a Result of Intensive Plipd–Lowering Therapy in Men with High Levels of Apolipoprotein B", N. Engl. J. Med. 323, No. 19, 1289–98, 1990.
Fawcett, J.P., et al, "Does Cholesterol Depletion Have Adverse Effects on Blood Rheology?", Angiology 45, No. 3 199–206, 1994.
Pan, H.Y. "Clinical pharmacology of pravastatin, s selective inhibitor of HMG–CoA reductase", Eur. J. Clin. Pharmacol. 40, Suppl. 1, 515–518, 1991.
Bo, M. et al, "One–Year Experience in the Treatment of Elderly Hypercholesterolemic Patients with Pravastatin", Curr. Ther. Res. 50, No. 2, 151–158, 1991.
Lancet 338, No. 8778, 1339, 1991.
Br. J. Haematol. 80, Supl 1, 35, 1992.
J. Am. Col. Cardiol. 23, Feb. 1994: 1A–484A, Spec. Issue 131 A.
Egashira, K. et al, "Reduction in Serum Cholesterol With Pravastatin Improves Endothelium–Dependent Coronary Vasomotion in Patients With Hypercholesterolemia", Circulation 89, No. 6. 2519–24, 1994.

* cited by examiner

Primary Examiner—Edward J. Webman

(57) ABSTRACT

A pharmaceutical composition is provided which is useful for cholesterol lowering and reducing the risk of a myocardial infarction, which includes a statin, such as pravastatin, lovastatin, simvastatin, atorvastatin, cerivastatin or fluvastatin, in combination with aspirin, in a manner to minimize interaction of aspirin with the statin and minimize side effects of aspirin. A method for lowering cholesterol and reducing risk of a myocardial infarction employing such composition is also provided.

16 Claims, No Drawings

PHARMACEUTICAL COMPOSITION CONTAINING A COMBINATION OF A STATIN AND ASPIRIN AND METHOD

FIELD OF THE INVENTION

The present invention relates to a pharmaceutical composition which includes a statin cholesterol lowering agent and aspirin in a manner to minimize interaction of aspirin with the statin, for use in lowering cholesterol and reducing risk of a myocardial infarction, and to a method for lowering cholesterol and reducing risk of a myocardial infarction employing such composition.

BACKGROUND OF THE INVENTION

The use of aspirin for reducing the risk of a myocardial infarction and the use of statins for lowering cholesterol and preventing or treating atherosclerosis and cardiovascular disease and cerebrovascular disease are well documented. In fact, it is not uncommon that patients having elevated cholesterol levels who are at high risk for a myocardial infarction take both a statin and aspirin. However, use of both a statin and aspirin may require special care to insure that drug interaction, including physical and chemical incompatibility, and side effects, are kept to a minimum while achieving maximum benefit from these drugs.

With regard to possible drug interaction, aspirin is an acid, while some of the statins, such as pravastatin, atorvastatin and cerivastatin, are alkali salts. Thus, mixing of such statins (alkali salts) with aspirin could result in aspirin hydrolysis as well as statin degradation. Pravastatin, on the other hand, is also a very acid labile compound. When pravastatin and aspirin are combined, the aspirin could cause pravastatin degradation which could result in lower bioavailability of pravastatin.

Aspirin is known for causing gastrointestinal bleeding when used for long-term therapy. It is therefore desirable in long-term aspirin therapy that the aspirin be provided in a form which minimizes side effects.

In view of the above, it is seen that there is a long-felt want in patients required to take both a statin and aspirin for a statin-aspirin formulation which provides for maximum cholesterol lowering and reduction of risk of a myocardial infarction without the undesirable side effects and drug interaction normally associated with use of such combination.

DESCRIPTION OF THE INVENTION

In accordance with the present invention, a pharmaceutical composition is provided which includes a statin cholesterol lowering agent and aspirin, which provides for maximum patient benefits including maximum cholesterol lowering and reduced risk of a myocardial infarction with minimal physical and chemical incompatibility (including minimal statin:aspirin interaction), and reduced side effects normally associated with use of such drugs.

In addition, in accordance with the present invention, a method is provided for lowering serum cholesterol, preventing or inhibiting or treating atherosclerosis, and/or reducing risk of or treating a cardiovascular event or disease including coronary artery disease and cerebrovascular disease, wherein a pharmaceutical composition containing a combination of a statin cholesterol lowering agent and aspirin in a single dosage form, in a manner so as to minimize interaction of the statin and aspirin, is administered to a patient in need of treatment.

Preferred pharmaceutical compositions of the present invention may take the form of several different embodiments. Thus, in one embodiment of the present invention, a pharmaceutical composition is provided wherein the statin (including any statin cholesterol lowering agent) and aspirin are formulated together in a single tablet. The tablet of the invention is preferably in the form of a bilayered tablet which includes a first layer and a second layer. Aspirin, in the form of granules of preselected size will be present in the first layer together with optional excipients as described hereinafter, while the statin will be present in the second layer which optionally may include one or more buffering agents (as necessary to prevent undesirable statin/aspirin interaction) and optionally one or more excipients as described hereinafter.

In addition, the bilayered tablet of the invention may include an outer protective coating or finishing layer as described hereinafter.

Another embodiment of the present invention comprises a cored tablet which includes a core and a buffering layer or outer coat which can be compressed onto the core as a dry coat. The core will preferably include compressed aspirin granules while the buffering layer or outer coat will include a statin (including any statin cholesterol lowering agent) together with one or more buffering agents and optional excipients.

Provision of aspirin in the core and statin in the buffering layer will effectively reduce the aspirin side effects and also minimize drug incompatibilities while providing maximum efficacy.

The so-described cored tablet may also optionally include an outer protective coating or finishing layer as described hereinafter.

In addition, in accordance with the present invention, a pharmaceutical composition is provided which is in the form of a tablet or capsule which includes a mixture of aspirin granules having an enteric coating and particles or granules of a statin. Such a combination will provide maximum efficacy while minimizing side effects resulting from prolonged aspirin therapy.

In the above embodiment containing enteric coated aspirin, the statin may include any statin cholesterol lowering agent, but preferably is simvastatin, lovastatin or cerivastatin.

In yet another embodiment of the pharmaceutical composition of the present invention, enteric coated aspirin granules as described above may be further coated with a protective coating or finishing layer. The double coated particles of aspirin can be mixed with any statins such as pravastatin, atorvastatin, simvastatin, lovastatin, and cerivastatin powders or granules, and the mixture can be encapsulated or tableted as described herein. In such case, further coating of the enteric coated aspirin particles is desired to minimize interaction of alkaline pravastatin, atorvastatin or cerivastatin with enteric coated aspirin. This combination will protect the integrity of the enteric coat and minimize the side effects normally resulting from prolonged aspirin therapy. The aspirin and the statin granules do not need to be mixed together; these can even be encapsulated separately into the same capsule shells in two shots.

Another embodiment of the pharmaceutical composition of the invention includes granules of enteric coated aspirin and enteric coated statin (including any statin cholesterol lowering agent), in the same dosage form such as compressed tablets or capsules.

The tablets containing the enteric coated granules of aspirin and statin may also include an outer protective coating or finishing layer.

In a further embodiment of the pharmaceutical composition of the invention, where aspirin side effects are not an issue, for example, where low dose aspirin is present (81 mg or less), the composition of the invention may comprise a mixture of aspirin granules and statin (including any statin cholesterol lowering agent, preferably, simvastatin, lovastatin or enteric coated particles of pravastatin or particles of pravastatin, atorvastatin and cerivastatin containing an outer protective coating or finishing layer); the above mixture may take the form of compressed tablets or capsules (where the mixture can be encapsulated separately in two shots in the same capsule shells).

DETAILED DESCRIPTION OF THE INVENTION

The pharmaceutical composition of the invention which includes a combination of a statin and aspirin is effective in preventing, reducing and/or treating elevated cholesterol levels (such as in hypercholesterolemia), atherosclerosis, cardiovascular events and disease including coronary events and cerebrovascular events, and coronary artery disease and/or cerebrovascular disease.

The terms "cardiovascular event(s)" and "cardiovascular disease" as employed herein refer to coronary and/or cerebrovascular event(s) and disease including primary myocardial infarction, secondary myocardial infarction, myocardial ischemia, angina pectoris (including unstable angina), congestive heart failure, sudden cardiac death, cerebral infarction, cerebral thrombosis, cerebral ischemia, transient ischemic attack and the like.

The term "coronary artery disease" (CAD) as employed herein refers to diseases including atherosclerosis of the coronary arteries, previous myocardial infarction, ischemia, angina pectoris and/or heart failure.

The term "cerebrovascular disease" as employed herein refers to diseases including atherosclerosis of the intracranial and/or extracranial arteries, cerebral infarction, cerebral thrombosis, cerebral ischemia, stroke, and/or transient ischemic attacks.

Aspirin will preferably be employed in the form of salicylic acid acetate also referred to as acetylsalicylic acid.

The pharmaceutical composition of the invention in the form of a tablet or capsule will include aspirin in amounts from about 10 to about 800 mg, preferably 50 to about 650 mg.

The aspirin for use in forming the pharmaceutical composition of the invention will preferably be in the form of granules having an average particle size within the range from about 10 $\mu$m to about 2 mm, more preferably from about 0.25 mm to about 1.0 mm.

Statin cholesterol lowering agents suitable for use herein will include HMG CoA reductase inhibitors such as pravastatin, lovastatin, simvastatin, atorvastatin, fluvastatin, cerivastatin and other statins such as fluindostatin and preferably pravastatin, simvastatin, atorvastatin or cerivastatin.

The pharmaceutical composition of the invention will contain a statin such as pravastatin, lovastatin, simvastatin, atorvastatin, fluvastatin or cerivastatin in an amount as normally employed for such statin as exemplified in the 52nd edition of the Physician's Desk Reference (PDR) (1998). Thus, depending upon the particular statin, it may be employed in amounts within the range from about 0.1 mg to 2000 mg per day in single or divided doses, and preferably from about 0.2 to about 200 mg per day. Most preferably for pravastatin, a daily dosage of 10 to 40 mg may be employed; for lovastatin, a daily dosage of 10 to 80 mg may be employed, for simvastatin a daily dosage of 5 to 40 mg may be employed; for atorvastatin, a daily dosage of 10 to 80 mg may be employed, for fluvastatin, a daily dosage of 20 to 80 mg may be employed; and for cerivastatin, a daily dosage of 0.2–0.3 mg may be employed.

In forming the pharmaceutical composition of the invention in the form of a bilayered tablet, the first layer containing aspirin will also preferably include bulking agents such as lactose, microcrystalline cellulose, wood cellulose, corn starch, modified corn starch, calcium phosphate, sugar, dextrose, mannitol or sorbitol. The bulking agent will be present in an amount from about 1 to about 90%, preferably from about 5 to about 85% by weight of the first layer containing aspirin.

The first layer may also include a tabletting lubricant, such as zinc stearate, magnesium stearate, calcium stearate, talc, carnauba wax, stearic acid, palmitic acid or hydrogenated vegetable oils and fats, in an amount within the range from about 0.01 to about 4%, and preferably 0.02 to about 2% by weight of the first layer.

The second layer of the bilayered tablet containing statin cholesterol lowering agent will usually include a bulking agent such as lactose, microcrystalline cellulose, modified corn starch, calcium phosphate or other bulking agent as set out above for the first layer, in an amount within the range from about 1 to about 90%, preferably from about 5 to about 85% by weight of the second layer. In addition, the second layer may include a binder such as corn starch, pregelatinized starch, polyvinyl pyrrolidone (PVP), hydroxypropylmethyl cellulose (HPMC), ethyl cellulose, cellulsoe acetate and the like, in an amount within the range from about 0.5 to about 20%, preferably from about 1 to about 10% by weight of the second layer, and a tabletting lubricant such as magnesium stearate, zinc stearate, or other lubricant as set out above with respect to the first layer in an amount from about 0.01 to about 4%, preferably from about 0.02 to about 2% by weight of the second layer.

The buffering agents present in the second layer may include conventional acid buffers such as calcium carbonate, magnesium oxide, magnesium carbonate, magnesium hydroxide, aluminum hydroxide, dihydroxyaluminum sodium carbonate, aluminum magnesium hydroxide sulfate or aluminum hydroxide magnesium carbonate co-dried gel, or mixtures of one or more thereof, in amounts as needed to insure that the aspirin will be sufficiently buffered to inhibit GI side effects. Thus, amounts of buffering agent within the range from about 10 to about 1000 mg, preferably from about 50 to about 500 mg will be employed depending upon the amount of aspirin present in the first layer.

In forming the bilayered tablet of the invention, the first layer containing aspirin may be prepared by conventional wet granulation or dry granulation (compaction) techniques.

The second layer containing statin and buffers may be prepared by conventional wet granulation or dry granulation (compaction) techniques.

The first and second layers may then be compressed and combined to form a bilayered tablet employing conventional bilayer tabletting equipment.

Other conventional ingredients which may optionally be present in either of the two layers include preservatives, stabilizers, anti-adherents or silica flow conditioners or glidants, such as Syloid brand silicon dioxide as well as antioxidants such as Vitamin E, Vitamin C, and folic acid, Vitamin $B_6$ and Vitamin $B_{12}$.

The bilayer tablet of the invention may also include an outer protective coating layer which may comprise from 0 to about 15% by weight of the bilayer tablet. The outer protective coating layer which is applied over the bilayered tablet may comprise any conventional coating formulations and will include one or more film-formers or binders, such as a hydrophilic polymer like hydroxy-propylmethyl cellulose (HPMC) and a hydrophobic polymer like ethyl cellulose, cellulose acetate, polyvinyl alcohol-maleic anhydride copolymers, acrylic copolymers, β-pinene polymers, glyceryl esters of wood resins and the like, and one or more plasticizers, such as polyethylene glycol, triethyl citrate, diethyl phthalate, propylene glycol, glycerin, butyl phthalate, castor oil and the like.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

The pharmaceutical composition of the invention in the form of a cored tablet wherein the aspirin forms the core, and statin plus buffering agent are present in a surrounding coat layer, may be prepared employing conventional cored tablet technology. Thus, the aspirin containing core (including excipients and other ingredients as described for the first layer in the bilayered tablet of the invention) may be formed in a manner similar to the first layer of the bilayered tablet as described hereinbefore. The buffering layer containing statin as well as excipients and other ingredients (as described hereinbefore for the second layer of the bilayered tablet of the invention) may be compressed onto the core as a dry coat.

The so-formed cored tablet may be coated with an outer protective coating layer as described above for the bilayered tablet.

Another embodiment of the pharmaceutical composition of the invention is formed of tablets or capsules containing a mixture of enteric coated aspirin granules, and a statin such as lovastatin, simvastatin or cerivastatin, which may be in the form of a tablet or capsule.

The aspirin granules can be coated with conventional enteric polymers coatings in aqueous or non-aqueous systems. For example, Eudragit L-30D-55 (acrylic acid copolymers-Rohm Pharma) (5 to 25% solids) containing 10 to 15% of diethylphthlate (w/w) as plasticizer can be used in an aqueous system.

Other conventional enteric polymer coating systems may be employed such as Eudragit R and S series resins, (acrylic acid copolymers-Rohm Pharma), cellulose acetate phthalate, cellulose acetate maleate, cellulose acetate succinate, hydroxypropylmethyl cellulose phthalate, hydroxypropylmethylcellulose acetate succinate, and the like, and a suitable plasticizer such as triethyl citrate, diethyl phthalate, tributyl citrate, triacetin, dibutyl phthalate, dibutyl sebicate, Myvacet 940, and other commonly used plasticizers as may be suitable for particular enteric polymers can be used. It will be appreciated that any polymer with suitable plasticizer can be used in aqueous or non-aqueous system to form an enteric coating on the aspirin granule or particle.

In another embodiment of the pharmaceutical composition of the invention, the enteric coated aspirin granules described above may be further coated with an outer protective finishing coat or layer as described hereinbefore.

The double coated aspirin granules can be mixed with a statin such as pravastatin, atorvastatin, simvastatin, lovastatin, fluvastatin or cerivastatin powders or granules and the mixture can be encapsulated or tableted as described above.

In yet another embodiment of the pharmaceutical composition of the invention, aspirin is enteric coated as described above and the statin (pravastatin, simvastatin, lovastatin, atorvastatin, fluvastatin and cerivastatin) can optionally be enteric coated. The statins can be coated in the form of pure drugs or after spheronization or agglomeration. The particles for coating do not need to be perfectly spherical. These could be rods or irregular particles. The enteric coated particles of the two drugs (aspirin and statin) can be tableted or encapsulated together. As described above, appropriate excipients (fillers, binders, disintegrants, and lubricant, etc.) can be used to facilitate tabletting. This statin:aspirin combination will minimize side effects of aspirin, and eliminate chemical incompatibility.

If, aspirin side effects are not an issue, especially at lower (e.g., 80 mg) aspirin dosages, then aspirin granules (including uncoated aspirin) can be mixed with simvastatin, lovastatin and fluvastatin powder or granules for tabletting or for encapsulating.

In yet another embodiment, aspirin granules can be mixed with enteric coated particles of pravastatin, cerivastatin and atorvastatin and the mixture can be tableted or encapsulated or the two granules can be encapsulated in two shots in the same capsule shells.

In carrying out the method of the present invention, the pharmaceutical composition of the invention containing the combination of the statin cholesterol lowering drug and aspirin may be administered to mammalian species, such as monkeys, dogs, cats, rats, humans, etc., and, as described hereinbefore, may be incorporated in a tablet or capsule. The above dosage forms will also include the necessary carrier material, excipient, lubricant, buffer, antibacterial, bulking agent (such as mannitol), anti-oxidants such as Vitamin C and Vitamin E, as well as Vitamin $B_6$, Vitamin $B_{12}$, folic acid, sodium bisulfite, and the like.

The dose administered must be adjusted according to age, weight and condition of the patient, as well as the route of administration, dosage form and regimen and the desired result.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing the active substances in the ranges described above, with the remainder being a physiologically acceptable carrier of other materials according to accepted pharmaceutical practice. These tablets can, of course, be scored to provide for fractional doses in some cases. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

In general, formulating the compositions, as described herein, the active substances, in the amounts described above, are compounded as described herein (according to accepted pharmaceutical practice) with a physiologically acceptable vehicle, carrier, excipient, binder, preservative, stabilizer, flavor, etc., in the particular type of unit dosage form.

Illustrative of the excipients which may be incorporated in tablets are the following: a binder such as gum tragacanth, acacia, corn starch or gelatin; an excipient such as dicalcium phosphate or cellulose; a disintegrating agent such as corn starch, potato starch, alginic acid, sodium starch glycolate or the like; a lubricant such as stearic acid, zinc stearate or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. As indicated, various other materials may be present as coatings or to otherwise modify the physical form of the dosage unit. For instance, tablets or capsules may be coated with shellac, sugar or both. A syrup of elixir may contain the active compounds, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for cardiovascular events and disease including coronary artery disease and/or cerebrovascular disease remains or the symptoms continue. Sustained release forms of such formulations which may provide such amounts daily, biweekly, weekly, monthly and the like may also be employed. A dosing period of at least 10 days are required to achieve minimal benefit.

The following Examples represent preferred embodiments of the present invention.

Formulations suitable for oral administration are prepared as described below.

EXAMPLE 1

A bilayered tablet containing aspirin in a first layer and pravastatin in a second layer as described below may be prepared as follows.

| General Formula: | |
| --- | --- |
| First Layer: | Amount or % in First Layer |
| Aspirin granulation | 80 mg–325 mg |
| Lactose/microcrystalline Cellulose granulation* | qs |
| Zinc Stearate | 0.1%–0.5 |
| Second Layer: | Amount in Second Layer |
| Calcium Carbonate | 50 mg–250 mg |
| Magnesium Oxide | 50 mg–100 mg |
| Magnesium Carbonate | 25 mg–50 mg |
| Corn Starch | 25 mg–50 mg |

-continued

| General Formula: | |
| --- | --- |
| Pravastatin | 20 mg–40 mg |
| Magnesium stearate | 0.2%–0.5% |

*This is an inert granulation just for the purpose of bulking, if necessary. This will contain 50%–90% lactose anhydrous, 10%–50% microcrystalline cellulose, and 0.1%–0.5% zinc stearate. These ingredients are blended, and appropriate size granules are prepared by conventional dry granulation process. (This being just an inert granulation, any other excipient can be used to prepare granules for bulking by dry or wet granulation processes, so that the granules do not have alkalizing agent and also do not contain excessive moisture and are compatible with aspirin granules. These bulking granules must have enough compatibility to allow compression of two layer tablets).

Procedure

The aspirin granulation in the first layer is blended with sufficient quantity of the lactose/microcrystalline cellulose granulation as necessary to bulk up in order to have sufficient granulation to compress a satisfactory layer. The aspirin granules along with the bulking granules are blended with zinc stearate as a lubricant. Zinc stearate can be replaced with other non-alkaline lubricants, i.e., Lubritab® or other high melting point hydrogenated powdered waxes.

Ingredients in the second layer are wet granulated using starch paste or other wet granulating materials, for example, PVP or HPMC, or can be dry granulated by compaction. The granules can be sized and lubricated. The two tablet layers are compressed using appropriate conventional tools and a suitable bilayer tabletting press, to form the bilayered tablet of the invention.

The quantity of the buffering agents used in the second layer can be adjusted as necessary to minimize gastrointestinal side effects. It should be understood that these buffering agents can be replaced with other suitable buffering agents, if desired.

The so-formed bilayered tablets may be coated with HPMC (hydroxypropylmethylcellulose) or commercially available Opadry® clear or Dri Klear® (HPMC) or any of these with any desired color. This coat is not limited to HPMC based coats only. Polymers, i.e., Eudragit E30D (acrylic acid copolymer) and others can also be used to give the tablets a finishing coat.

| Coating Formula (example): | |
| --- | --- |
| Opadry ® clear | 10%–30% |
| Purified water | qs |

Procedure

Opadry® is dispersed in water to prepare a dispersion of 10%–30% solids*. This dispersion is used for coating the above tablets using conventional coating equipment. The coating of 0.2%–2% or any desired level (based on the weight of the finished coated bilayered tablet) can be applied to the bilayered tablet employing conventional techniques.

*Antifoam emulsion at a level of 0.1 to 2% of solids, can also be included in the formulation.

The so-formed tablets provide maximum benefits while minimizing drug interaction and other undesirable side effects.

It will be understood that pravastatin contained in the buffered layer of the bilayered tablet of the invention may be replaced with equivalent cholesterol lowering amounts of simvastatin, lovastatin, atorvastatin, cerivastatin or fluvastatin.

EXAMPLE 2

Tablets or capsules containing enteric coated aspirin and a statin, which preferably is simvastatin, lovastatin or cerivastatin, having the following composition are prepared as described below.

| General Formula: | |
| --- | --- |
| Aspirin particles | 80 mg–325 mg |
| Eudragit L-30D-55 | qs |
| Diethyl Phthalate | qs |
| Statins (simvastatin, lovastatin, or cerivastatin) | Desired Dose (as per PDR) |

Procedure

Aspirin particles are coated with enteric polymers in aqueous or non-aqueous systems. Eudragit L-30D-55 containing 10%–15% of diethyl phthalate (w/w) is used in an aqueous system. The coating suspension is prepared having solid contents of 10%–30%.

To prepare the coating suspension, diethyl phthalate is added to the Eudragit L-30D-55 and the contents stirred till diethyl phthalate is completely dissolved. This is diluted with water to obtain the suspension with desired solid contents. Using this enteric coating suspension, the aspirin particles are coated in a fluid bed coating system using a Wurster insert or with top spray coating, so that aspirin particles of enteric quality can be produced. The enteric coated particles are mixed with statin powders or granules and the mixtures are encapsulated or tableted using appropriate excipients (fillers, binder, disintegrants, and lubricants). Any of the listed statin can be selected at its desired dose level along with the desired aspirin dose.

The statins can also be granulated, and the statin granules and the enteric coated aspirin granules can be filled separately into the same capsule shell. Statin granules can be prepared by dry or wet granulation processes, using suitable conventional excipients as is well known in the pharmaceutical field.

The above formulations provide maximum benefit while minimizing undesirable side effects and incompatibilities.

EXAMPLE 3

A cored tablet containing an aspirin core and a buffered coating thereon containing a statin having the following composition is prepared as described below.

| General Formula: | |
| --- | --- |
| Core Layer: | Amount or % in Core Layer |
| Aspirin granulation | 80 mg–325 mg |
| Lactose/microcrystalline Cellulose granulation* | qs |
| Zinc Stearate | 0.1%–0.5 |
| Outer Layer: | Amount in Second Layer |
| Calcium Carbonate | 50 mg–250 mg |
| Magnesium Oxide | 50 mg–100 mg |
| Magnesium Carbonate | 25 mg–50 mg |
| Corn Starch | 25 mg–50 mg |
| Pravastatin | 20 mg–30 mg |
| Magnesium stearate | 0.2%–0.5% |
| Filler/Binder** | qs |

*This is an inert granulation just for the purpose of bulking, if necessary. This will contain 50%–90% lactose anhydrous, 10%–50% microcrystalline cellulose, and 0.1%–0.5% zinc stearate. These ingredients are blended, and appropriate size granules are prepared by conventional dry granulation process. (This being just an inert granulation, any other excipient can be used to prepare granules for bulking by dry or wet granulation processes, so that the granules do not have alkalizing agent and also do not contain excessive moisture and are compatible with aspirin granules. These bulking granules must have enough compatibility to allow compression of two layer tablets).
**The Filler/Binder may be any known fillers or tablet binders, such as lactose, microcrystalline cellulose, modified starch, calcium phosphate and the like.

Procedure

The aspirin granulation for the core is blended with sufficient quantity of the lactose/microcrystalline cellulose granulation as necessary to bulk up in order to have sufficient granulation to compress a satisfactory core. The aspirin granules along with the bulking granules are blended with zinc stearate as a lubricant. Zinc stearate can be replaced with other non-alkaline lubricants, i.e., Lubritab® or other high melting point hydrogenated powdered waxes.

Ingredients for the outer layer are wet granulated using starch paste or other wet granulating materials, for example, PVP or HPMC, or can be dry granulated by compaction. The granules can be sized and lubricated. The dry coated tablets can be compressed using appropriate tools and a suitable dry coating tabletting press.

The quantity of the buffering agents used in the outer layer can be adjusted as in Example 1. Other known buffering agents may be used as well.

What is claimed is:

1. A pharmaceutical composition comprising a statin cholesterol lowering agent and aspirin in a formulation to reduce statin:aspirin interaction wherein the statin and aspirin are formulated together in a bilayered tablet, the aspirin being present in a first layer, and the statin being present in a second layer.

2. The pharmaceutical composition as defined in claim 1 wherein the layer containing the statin also includes one or more buffering agents.

3. The pharmaceutical composition as defined in claim 1 wherein the tablet includes a core and a coating layer surrounding said core and wherein one of the statin and aspirin is present in the core and the other is present in the coating layer surrounding the core.

4. The pharmaceutical composition as defined in claim 3 wherein the aspirin is present in the core and the statin is present in the coating layer.

5. The pharmaceutical composition as defined in claim 4 wherein the coating layer also includes one or more buffering agents.

6. The pharmaceutical composition as defined in claim 1 wherein the statin is pravastatin, lovastatin, simvastatin, fluvastatin, atorvastatin or cerivastatin.

7. The pharmaceutical composition as defined in claim 1 further including an outer protective coating or finishing layer surrounding said tablet.

8. The pharmaceutical composition as defined in claim 1 wherein the aspirin is in the form of enteric coated aspirin granules.

9. The pharmaceutical composition as defined in claim 1 in the form of a bilayered tablet which comprises a first layer comprising aspirin granules and one or more excipients, and a second layer comprising a statin and one or more buffering compounds and one or more excipients.

10. The pharmaceutical composition as defined in claim 9 wherein the first layer comprises aspirin granules, one or more bulking agents and optionally a lubricant, and the second layer comprises a statin, optionally a wet granulating agent, one or more buffering compounds selected from the group consisting of calcium carbonate, magnesium oxide, magnesium carbonate and mixtures thereof, and optionally magnesium stearate.

11. The pharmaceutical composition as defined in claim 9 further including an outer protective coating surrounding said bilayered tablet.

12. The pharmaceutical composition as defined in claim 1 further including an antioxidant.

13. The pharmaceutical composition as defined in claim 12 wherein the antioxidant is vitamin C and/or vitamin E.

14. A method for lowering serum cholesterol or preventing or inhibiting or treating atherosclerosis or reducing risk of or treating a cardiovascular event or disease, coronary artery disease or cerebrovascular disease, which comprises administering to a patient in need of treatment a therapeutically effective amount of a pharmaceutical composition according to claim 4.

15. The method as defined in claim 14 wherein the statin employed is pravastatin, lovastatin, simvastatin, atorvastatin, fluvastatin or cerivastatin.

16. A pharmaceutical composition comprising pravastatin and aspirin in a formulation to reduce pravastatin:aspirin interaction wherein the pravastatin and aspirin are formulated together in a bilayered tablet, the aspirin being present in a first layer, and the pravastatin being present in a second layer.

* * * * *